United States Patent
Lindsay

[19]

[11] Patent Number: 5,871,693
[45] Date of Patent: Feb. 16, 1999

[54] MODULAR BLOOD TREATMENT CARTRIDGE

[75] Inventor: Erin J. Lindsay, Manchester, Mich.

[73] Assignee: Minnesota Mining and Manufacturing Company, St. Paul, Minn.

[21] Appl. No.: 659,808

[22] Filed: Jun. 7, 1996

[51] Int. Cl.$^6$ ............................. A61M 1/07; A61M 37/00
[52] U.S. Cl. ..................................... 422/44; 604/5; 604/6
[58] Field of Search .................................. 422/44; 604/5, 604/6

[56] References Cited

U.S. PATENT DOCUMENTS

| | | | |
|---|---|---|---|
| 3,507,395 | 4/1970 | Bentley | 210/443 |
| 3,701,433 | 10/1972 | Krakauer et al. | 210/436 |
| 3,742,934 | 7/1973 | Holbrook et al. | 128/2 |
| 3,768,653 | 10/1973 | Brumfield | 210/188 |
| 3,803,810 | 4/1974 | Rosenberg | 55/159 |
| 3,891,416 | 6/1975 | Leonard et al. | 55/178 |
| 3,892,534 | 7/1975 | Leonard | 23/258.5 |
| 3,927,980 | 12/1975 | Leonard | 23/258.5 |
| 3,993,461 | 11/1976 | Leonard et al. | 55/178 |
| 4,054,523 | 10/1977 | Ingenito et al. | 210/188 |
| 4,151,088 | 4/1979 | Wolf, Jr. et al. | 210/180 |
| 4,157,965 | 6/1979 | Raible | 210/305 |

(List continued on next page.)

FOREIGN PATENT DOCUMENTS

| | | | |
|---|---|---|---|
| 0 207 304 | 1/1987 | European Pat. Off. | A61M 1/00 |
| 0 312 101 | 4/1989 | European Pat. Off. | A61M 5/14 |
| 0 313 107 | 4/1989 | European Pat. Off. | A61M 1/00 |
| 0 355 785 | 2/1990 | European Pat. Off. | A61M 1/36 |
| 0 437 957 | 7/1991 | European Pat. Off. | A61M 1/36 |
| 777.243 | 2/1935 | France | 7/3 |
| WO 93/25249 | 12/1993 | WIPO | A61M 1/36 |
| WO 95/11709 | 5/1995 | WIPO | A61M 1/36 |
| WO 96/00593 | 1/1996 | WIPO | A61M 1/36 |

OTHER PUBLICATIONS

"Bard William Harvey HF–5701 Membrane Oxygenator—Directions for use"; Bard Cardiopulmonary Division—C.R. Bard, Inc.; R3355/6–92/B Month Unavailable Year Not Known.

"Bard William Harvey H–4700 Series Cardiotomy Reservoir—Directions for Use"; Bard Cardiosurgery Division—C.R. Bard, Inc. Month Unavailable Year Not Known.

(List continued on next page.)

*Primary Examiner*—Robert J. Warden
*Assistant Examiner*—Alex Noguerola
*Attorney, Agent, or Firm*—Robert W. Sprague; Karl G. Schwappach; Stephen W. Bauer

[57] ABSTRACT

A modular blood treatment system with a blood treatment cartridge having a blood treatment media receiving opening defining an entrance of a first chamber. The first chamber defines a first interior space and a second interior space. At least one cardiotomy blood sucker port is in fluid communication with the first interior space via a cardiotomy manifold. The cardiotomy manifold preferably defines a downward curving surface from the at least one cardiotomy blood sucker port to the first interior space having a radius of about 2.54 to 7.62 cm. A venous blood inlet is in fluid communication with a second interior space within the interior space. A first blood treatment media is interposed between the first interior space and the second interior space. A second blood treatment media is interposed between the second interior space and the blood treatment media receiving opening. A blood storage section has an outlet port extends substantially across the blood treatment media receiving opening. In one embodiment, at least one blood diverter is located in the blood storage section to form two funnel-shaped blood flow channels between the blood treatment media opening and the outlet port. The funnel-shaped blood flow channels preferably define a first downward flow axis at an angle of about 20 to 24 degrees with respect to horizontal. The funnel-shaped blood flow channels preferably define a second downward flow axis at an angle from horizontal of about 3 to 7 degrees laterally from the first downward flow axis.

15 Claims, 11 Drawing Sheets

U.S. PATENT DOCUMENTS

| | | | |
|---|---|---|---|
| 4,164,468 | 8/1979 | Raible | 210/23 |
| 4,183,961 | 1/1980 | Curtis | 424/366 |
| 4,208,193 | 6/1980 | Munsch et al. | 55/36 |
| 4,243,531 | 1/1981 | Crockett et al. | 210/188 |
| 4,261,951 | 4/1981 | Milev | 422/46 |
| 4,336,224 | 6/1982 | Siposs | 422/46 |
| 4,422,939 | 12/1983 | Sharp et al. | 210/445 |
| 4,424,190 | 1/1984 | Mather, III et al. | 422/46 |
| 4,440,723 | 4/1984 | Gordon | 422/47 |
| 4,451,562 | 5/1984 | Elgas et al. | 435/2 |
| 4,466,888 | 8/1984 | Verkaart | 210/232 |
| 4,469,659 | 9/1984 | Carson et al. | 422/46 |
| 4,490,331 | 12/1984 | Steg, Jr. | 422/46 |
| 4,517,090 | 5/1985 | Kersten et al. | 210/493.2 |
| 4,568,367 | 2/1986 | Gremel et al. | 55/178 |
| 4,585,056 | 4/1986 | Oscarsson | 165/133 |
| 4,589,822 | 5/1986 | Clausen et al. | 415/170 |
| 4,606,698 | 8/1986 | Clausen et al. | 415/170 |
| 4,642,089 | 2/1987 | Zupkas et al. | 604/4 |
| 4,643,641 | 2/1987 | Clausen et al. | 415/170 |
| 4,656,004 | 4/1987 | Stewart | 422/46 |
| 4,664,682 | 5/1987 | Monzen | 55/178 |
| 4,668,394 | 5/1987 | Badolato et al. | 210/314 |
| 4,705,497 | 11/1987 | Shitaokoshi et al. | 604/4 |
| 4,737,139 | 4/1988 | Zupkas et al. | 604/4 |
| 4,743,371 | 5/1988 | Servas et al. | 210/188 |
| 4,756,705 | 7/1988 | Beijbom et al. | 604/4 |
| 4,818,490 | 4/1989 | Carson et al. | 422/46 |
| 4,846,800 | 7/1989 | Ouriel et al. | 604/4 |
| 4,876,066 | 10/1989 | Bringham et al. | 422/46 |
| 4,883,455 | 11/1989 | Leonard | 604/4 |
| 4,909,780 | 3/1990 | Ouriel et al. | 604/4 |
| 4,923,438 | 5/1990 | Vasconcellos et al. | 604/4 |
| 4,936,759 | 6/1990 | Clausen et al. | 417/423 |
| 5,034,188 | 7/1991 | Nakanishi et al. | 422/46 |
| 5,039,430 | 8/1991 | Corey, Jr. | 210/806 |
| 5,039,482 | 8/1991 | Panzani et al. | 422/46 |
| 5,043,140 | 8/1991 | Combs | 422/46 |
| 5,049,146 | 9/1991 | Bringham et al. | 604/4 |
| 5,078,677 | 1/1992 | Gentelia et al. | 604/4 |
| 5,087,250 | 2/1992 | Lichte et al. | 604/321 |
| 5,112,480 | 5/1992 | Hukasawa | 210/188 |
| 5,120,302 | 6/1992 | Vescovini et al. | 604/4 |
| 5,127,900 | 7/1992 | Schickling et al. | 604/4 |
| 5,149,318 | 9/1992 | Lindsay | 604/4 |
| 5,152,964 | 10/1992 | Leonard | 422/48 |
| 5,158,533 | 10/1992 | Strauss et al. | 604/4 |
| 5,160,332 | 11/1992 | Nomura | 604/405 |
| 5,162,101 | 11/1992 | Cosentino et al. | 422/46 |
| 5,167,921 | 12/1992 | Gordon | 422/46 |
| 5,192,439 | 3/1993 | Roth et al. | 210/485 |
| 5,211,913 | 5/1993 | Hagiwara et al. | 422/44 |
| 5,254,080 | 10/1993 | Lindsay | 604/4 |
| 5,270,005 | 12/1993 | Raible | 422/46 |
| 5,282,783 | 2/1994 | Lindsay | 604/4 |
| 5,304,164 | 4/1994 | Lindsay | 604/403 |
| 5,328,461 | 7/1994 | Utterberg | 604/80 |
| 5,382,407 | 1/1995 | Leonard | 422/48 |
| 5,399,156 | 3/1995 | Lindsay | 604/4 |
| 5,403,273 | 4/1995 | Lindsay | 604/4 |
| 5,411,705 | 5/1995 | Thor et al. | 422/45 |
| 5,472,605 | 12/1995 | Zuk, Jr. | 210/436 |
| 5,514,335 | 5/1996 | Leonard et al. | 422/46 |
| 5,543,062 | 8/1996 | Nishimura | 210/782 |

OTHER PUBLICATIONS

"Baxter Bentley Univox IC Open Membrane Oxygenation System—Instructions for use"; Baxter Healthcare Corporation; PN10AN7212–01 R1 Sep. 19, 1990.

"HSVRF Hardshell Venous Reservoir with Integral Cardiotomy Filter—Instructions for Use"; Shiley Incorporated; 1987; DP22–2025–001 (Nov. 1987).

"COBE Membrane Lung Ultra—Instructions for Use"; COBE; P/N 434197–333 Rev. B Year Not Known Month Unavailable.

"Now everyone can breathe easier—COBE CML"; COBE Laboratories; 1983.

"COBE VPCML Plus—The Variable Prime Membrane Oxygenator to Meet Your Neonatal, Infant and Pediatric Requirements . . . "; COBE Laboratories Month Available Year Not Known.

"New COBE VPCML—One Size Fits Small" COBE Laboratories; 1984.

"Making the best even better?"; COBE Laboratories, Inc.; 1986; 421–200–027 Month Unavailable.

Iatridis et al; "Range of usage for the Variable Prime Cobe Membrane Lund (VPCML)"; Perfusion 1986; 1:277–279 Month Unavailable.

Crockett et al.; "The Variable Prime Cobe Membrane Lung: first impressions"; Perfusion 1987; 2:205–12 Month Unavailable.

Iatridis; "Laboratory Evaluation of the Variable Prime Cobe Membrane Lung"; Proceedings of the American Academy of Cardiovascular Perfusion, vol. 6, Jan. 1985.

"For you, The GISH CAP–35 works"; GISH Biomedical, Inc. Month Unavailable Year Not Known.

"There's Nothing Safer Than Your Patient's Own Blood."; GISH Biomedical, Inc.; Year Not Known.

"Hemodynamic Duo", GISH Biomedical, Inc. Month Unavailable Year Not Known.

"GISH–ATR—Blood Recovery/Autotransfusion System—Directions for Use"; GISH Biomedical, Inc.; A14391–01 Month Unavailable Year Not Known.

"Cardiotomy Resrevoirs—Directions for Use"; Cardio Metrics Month Unavailable Year Not Known.

"Sarns Filtered Venous Reservoir"; 3M Health Care 1991; Form No. 78–8607–33712–9 Month Unavailable Year Not Known.

"When you bring efficiency to the surface . . . you can lower the prime."; 3M Health Care; 1990; Form No. 16088004 Rev. B Year Not Known.

"SMO/IR Sarns Membrane Oxygenator with Integral Reservoir–"; 3M Health Care; 1990; Form No. 78–8066–9350–9.

SMO/ICR Sarns Membrane Oxygenator with Integral Cardiotomy Reservoir; 3M Health Care; 1990; Form No. 78–806609349–1.

"Sarns SMO/ICR Membrane Oxygenator with Integral Cardiotomy Reservoir—Instructions"; 3M Health Care; Sep., 1990; Form No. 34–9998–9114–5 R/C.

"Biocor 200 High Performance Oxygenator—Maximum Performance. minimum Prime Volume. Minimum Surface Area."; Minntech Corporation Month Unavailable Year Not Known.

"Affinity Integrated CVR Membrane Oxygenator—Instructions for Use"; Avecor Cardiovascular; 141027–01 Month Unavailable Year Not Known.

Flyer entitled "Using Design to It's Full Potential"; Perfusion 9(6)1994; by Sorin Biomedica Month Unavailable.

Flyer entitled "Sorin Oxygenators Vital Details in Full Sight"; by Sorin Biomedica Month Unavailable Year Not Known.

Instructions for Use "Monolyth—Monolyth Integrated Membrane Lung"; by Sorin Biomedical; 1993 LC45–1000–001C(Nov. 1994).

"COBE CML Utra—When Priming Volume really counts . . ."; COBE Laboratories, Inc. 1989; 421–200–051 Month Unavailable.

"COBE—Membrane Lund (CML) Blood Oxygenator—Performance Characteristics"; COBE Laboratories, Inc. 1983 Month Unavailable.

"COBE CML—Blood Oxygenator with Integral Filter—Instructions for Use"; COBE Laboratories, Inc.; Oct., 1989; 434303–101 Rev. A Month Unavailable.

Reed et al.; "Cardioplumonary Bypass"; Second Edition, 1985; p. 337 showing a picture of an intersept cardiotomy reservoir.

Revised sketch (1 page) prepared Apr. 17, 1997 of the "Monolyth" integrated membrane lung available from Sorin Biomedica.

A sketch (3 figures, 1 sheet) prepared between Sep. 12–17, 1996 to help illustrate various details of the reservoir of a "Monolyth" Integrated Membrane Lung available from Sorin Biomedica.

T. Gourley et al., *Equipment Evaluation: Evaluation of the Sorin Monolyth Membrane Oxygenator*, Perfusion 1990; 5: 209–219 Month Unavailable.

Advertisement, "Enter the Monolyth Club . . . and get introduced to Monolyth the winner." by Sorin Biomedica (undated) Month Unavailable.

Sorin Biomedica publication, "Monolyth: Clinical and Technical documentation on Monolyth" (undated) Month Unavailable.

A copy of a computer printout indicating that a FDA 510(k) filing (No. K922933) on a Sorin Monolyth Integrated Membrane Lung was received at the FDA on Jun. 18, 1992 and decided on Nov. 30, 1992.

MODULAR BLOOD TREATMENT CARTRIDGE

FIELD OF THE INVENTION

The present invention relates to a modular blood treatment cartridge and a method of assembling the same, and in particular, to a blood treatment cartridge with a two-dimensional assembly process that facilitates automated assembly and substitution of a variety of blood treatment media. The present invention is also directed to a modular blood treatment cartridge with a high degree of biocompatibility and visibility.

BACKGROUND OF THE INVENTION

Various surgical procedures require interrupting the normal functioning of the heart and lungs of the patient. Some of the functions of these organs are temporarily replaced by an extracorporeal blood handling system. The main volume of the patient's blood, known as the venous return stream, is typically withdrawn from the patient through a venous cannula inserted into the right atrium. The blood handling system collects the volume of blood in a venous reservoir. The blood handling system serves to pump the blood, regulate the carbon dioxide and oxygen content, regulate the temperature, defoam and remove emboli and particulate matter using one or more filters. The blood is then returned to the patient through an aortic cannula inserted into the aorta distal to the heart.

Blood from the surgical field, known as cardiotomy blood, is typically drawn into a cardiotomy reservoir. The cardiotomy blood typically contains gas bubbles, fragments of tissue, bone chips, blood clots, surgical debris and other dangerous and undesirable contaminants. The cardiotomy reservoir defoams, filters and collects the cardiotomy blood prior to combining it with blood in the venous reservoir. The level of filtration required for cardiotomy blood is typically greater than that required for the relatively clean venous return stream.

The high level of filtration necessary for cardiotomy blood may cause damage to blood constituents, such as to due to sheer stress. Consequently, cardiotomy blood filtration is preferably performed separately from filtration of the relatively clean venous return stream. Integrated cardiotomy reservoirs (ICR) combine the treatment of both cardiotomy and venous blood streams.

Turbulent flow may develop at various locations within the blood handling system. Turbulent flow can cause bubbles to form in the blood and can increase the blood-to-air contact. Blood to air contact causes hemolysis of red blood cells. Hemolysis refers to the lysis or destruction of erythrocytes with the release of hemoglobin, resulting in a reduction in the ability of the blood to carry oxygen.

Blood handling systems can also have locations of blood stasis that can cause blood clotting or separation of blood components. Medical care providers are increasingly interested in viewing the condition of the blood throughout the entire blood circuit. Current blood treatment systems typically have internal regions that are not visible to the medical staff, such as the interior of cylindrically shaped filter media. Areas within the blood handling system that cannot be viewed by the medical staff may result in undetected blood stasis or clots.

Typical blood handling systems have a large number of discrete parts, requiring manual assembly, increasing the risk of assembly errors and increasing manufacturing costs. Manufacturing a variety of distinct extracorporeal blood handling systems with different blood treatment elements increases manufacturing and inventory costs. Variability between products also raises the risk of errors in assembly or marking of finished products, resulting in a potentially detrimental medical impact on the patient.

SUMMARY OF THE INVENTION

The present invention relates to a modular blood treatment cartridge and a method of assembling the same.

The present modular blood treatment system utilizes a blood treatment cartridge with a two-dimensional assembly process that facilitates automated assembly and substitution of a variety of blood treatment media.

The present invention is also directed to a modular blood treatment cartridge with a high degree of biocompatibility and visibility.

The modular blood treatment system defines a blood flow path for facilitating automated assembly along a single build axis. A blood treatment cartridge has a blood treatment media receiving opening that defines an entrance to a first chamber. The first chamber includes a first interior space and a second interior space. At least one cardiotomy blood sucker port is in fluid communication with the first interior space via a cardiotomy manifold. A venous blood inlet is in fluid communication with the second interior space. A first blood treatment media is interengaged with the blood treatment cartridge along the build axis. The first blood treatment media is preferably interposed between the first interior space and the second interior space. A second blood treatment media is interengaged with the blood treatment cartridge along the build axis. The second blood treatment media is preferably interposed between the second interior space and the blood treatment media receiving opening. A blood storage section is interengaged with the blood treatment cartridge along the build axis and extends substantially across the blood treatment media receiving opening. The blood storage section includes an outlet port.

The modular blood treatment system is preferably a transparent plastic material configured so that substantially the entire blood flow path is visible.

The blood treatment cartridge has a first ledge for receiving the first blood treatment media and a second ledge for receiving the second blood treatment media. The first ledge preferably defines a perimeter larger than the second ledge.

The first blood treatment media is a cardiotomy blood treatment media. The second blood treatment media is a venous blood treatment media. In one embodiment, the cardiotomy blood treatment media includes both a defoamer mesh and a filter media. The cardiotomy blood treatment media is a filter media with an average pore size of about 20 to 40 microns. The venous blood treatment media is preferably a defoamer media. A first frame preferably extends around a perimeter of the first blood treatment media. A second frame preferably extends around a perimeter of the second blood treatment media.

The blood storage section includes a blood diverter forming a pair of funnel-shaped blood flow channel extending between the blood treatment media opening and the outlet port. The funnel-shaped blood flow channels define a first downward flow axis at an angle of about 20 to 24 with respect to horizontal The funnel-shaped blood flow channel also defines a second flow axis perpendicular from the first flow axis extending downward from the blood diverter at an angle of about 3 to 7.

The cardiotomy manifold defines a downward curving surface extending from the at least one cardiotomy blood sucker port to the first interior space having a radius of about 2.54 to 7.62 cm. The opening in a blood sucker port is tangent to the downward curving surface of the cardiotomy manifold. The venous blood inlet includes a directionalized, low-velocity prime bowl for directing a portion of the blood flow path toward edges of the first chamber. The venous blood inlet has a cross-section at least four times greater than a cross-section of the venous blood inlet.

In an alternate embodiment, the blood storage section is a flexible blood reservoir in fluid communication with the outlet port.

In an alternate embodiment, the modular blood treatment system includes a blood treatment cartridge having a blood treatment media receiving opening defining an entrance of a first chamber. The first chamber includes a first interior space and a second interior space. At least one cardiotomy blood sucker port is in fluid communication with the first interior space via a cardiotomy manifold. A venous blood inlet is in fluid communication with a second interior space within the interior space. At least one cardiotomy blood treatment media is interposed between the first interior space and the second interior space. At least one venous blood treatment media is interposed between the second interior space and the blood treatment media receiving opening. A blood storage section extends substantially across the blood treatment media receiving opening. The blood storage section includes an outlet port. At least one blood diverter is located in the blood storage section for forming at least one funnel-shaped blood flow channel between the blood treatment media opening and the outlet port. The funnel-shaped blood flow channel defines a first downward flow axis at an angle of about 20 to 24 with respect to horizontal.

In an alternate embodiment, the modular blood treatment system includes a cardiotomy manifold defining a downward curving surface extending from the cardiotomy blood sucker ports to the first interior space. The downward curving surface has a radius of about 2.54 to 7.62 cm.

In another embodiment, the modular blood treatment system has a visible blood flow path. The transparent blood treatment cartridge has a blood treatment media receiving opening defining an entrance of a first chamber. The first chamber defines a first interior space and a second interior space. At least one cardiotomy blood sucker port is in fluid communication with the first interior space via a cardiotomy manifold. The venous blood inlet is in fluid communication with a second interior space within the interior space. At least one discontinuous cardiotomy blood treatment media is interposed between the first interior space and the second interior space so that the first interior space is visible through the transparent blood treatment cartridge. At least one discontinuous venous blood treatment media is interposed between the second interior space and the blood treatment media receiving opening so that the second interior space is visible through the transparent blood treatment cartridge. The transparent blood storage section extends substantially across the blood treatment media receiving opening.

As used herein:

Biocompatibility refers to a low-turbulent flow path that minimizes hemolysis and blood-air contact.

Initial Break Through Volume refers to the volume of fluid required before the fluid penetrates the filter media and reaches the output port in the reservoir. Initial break through volume is typically most significant when priming the modular blood treatment system.

Sucker Bypass refers to a condition where both the venous return stream and the cardiotomy blood stream both pass through the cardiotomy filters.

DETAILED DESCRIPTION OF THE PREFERRED EMBODIMENTS

Figure 1:
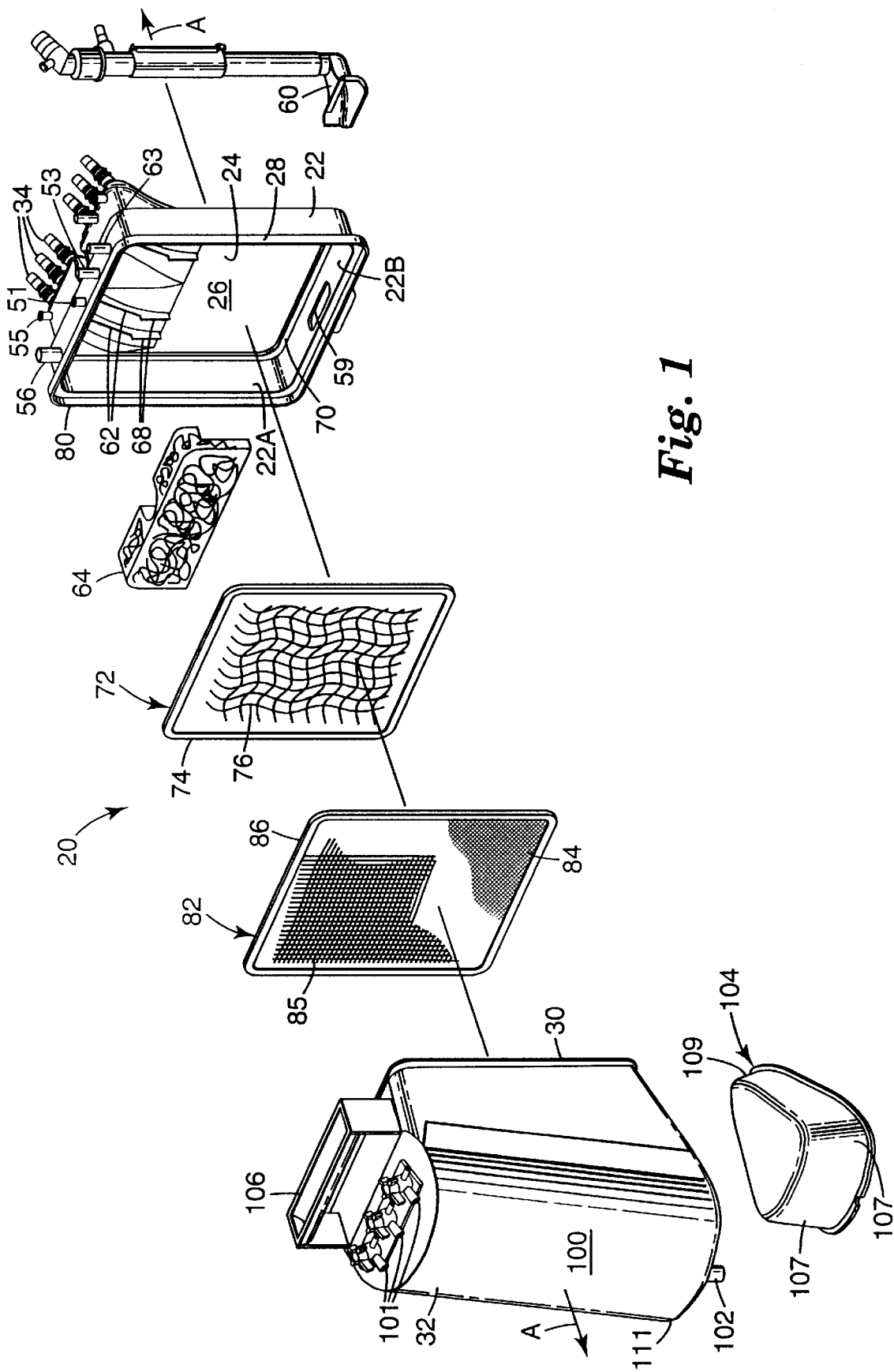
FIG. 1 is an exploded view of an exemplary modular blood treatment system.

FIGS. 1–6 illustrate one embodiment of the present modular blood treatment system 20. Blood treatment cartridge 22 has a blood treatment media receiving opening 24 defining an entrance to a chamber 26. A cartridge flange 28 extends around the perimeter of the blood treatment media opening 24 for engagement with a corresponding flange 30 on a front blood reservoir 32, as will be discussed in detail below.

Figure 4:
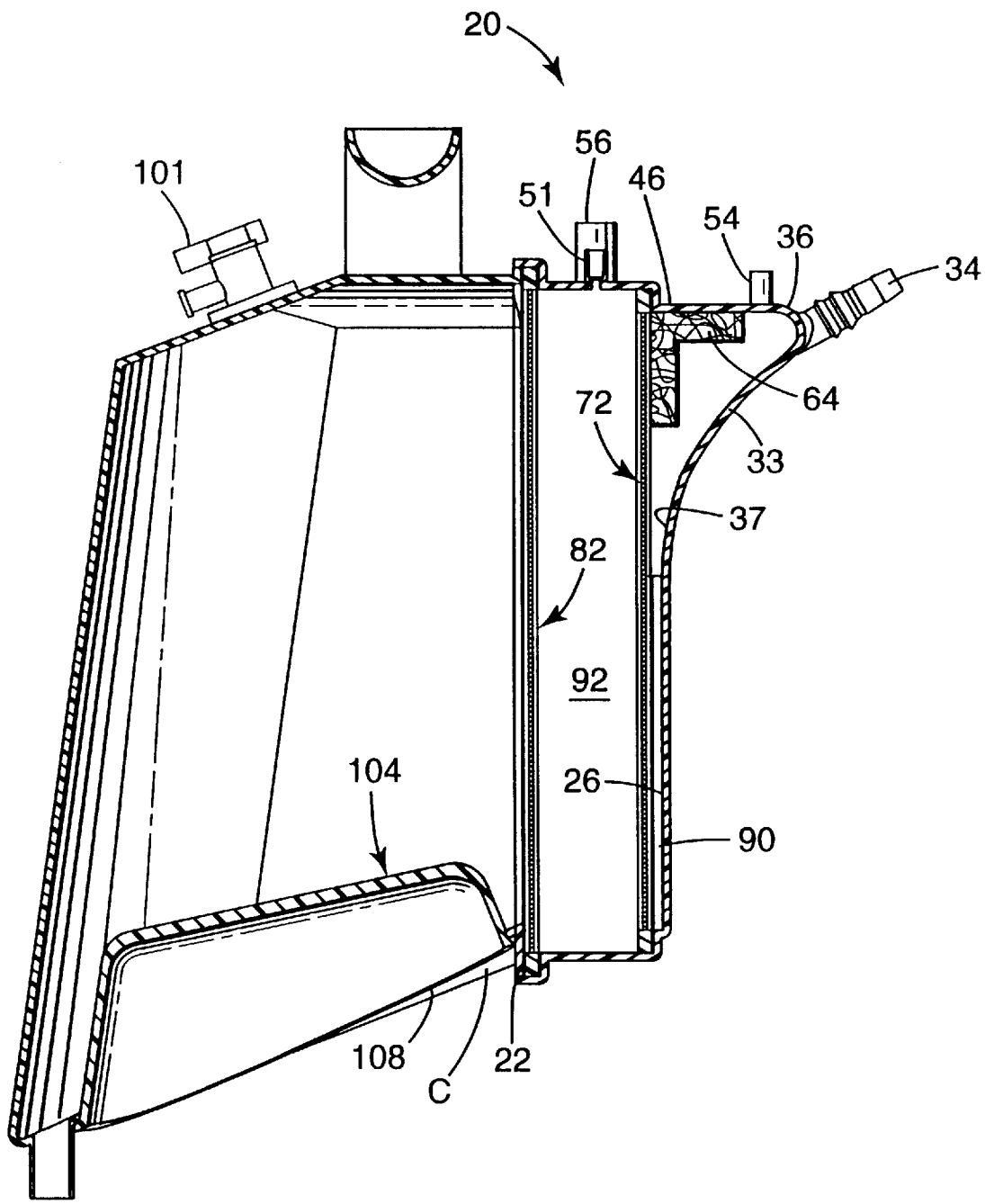
FIG. 4 is an alternate side sectional view of the modular blood treatment system of FIG. 1.
Figure 5:
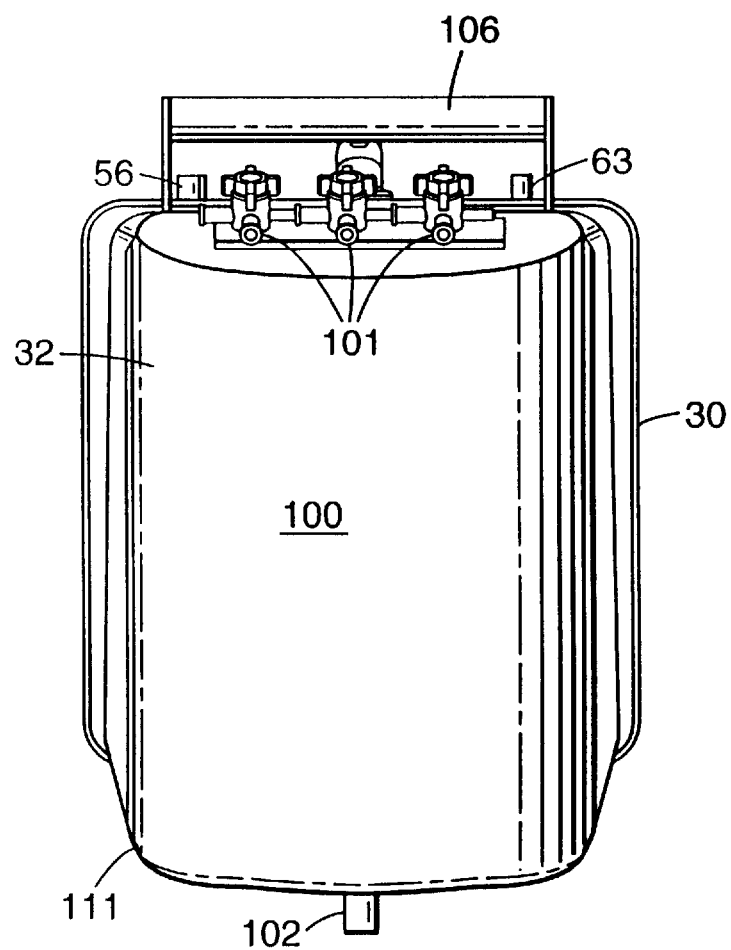
FIG. 5 is a front view of the modular blood treatment system of FIG. 1.

A series of sucker ports 34 are located along a top edge of the blood treatment cartridge 22. The sucker ports 34 are preferably connected to one or more lines of tubing conducting cardiotomy blood from the surgical site to the modular blood treatment system 20 (not shown). As best seen in FIG. 4, the blood sucker ports 34 are in fluid communication with a cardiotomy manifold 36 that leads to a separation chamber 37. The cardiotomy manifold 36 and sucker ports 34 define an arch 33 having a radius of curvature of about 3.8 cm (1.5 inches), and preferably in the range of 2.54 cm to 7.62 cm (1.0 inches to 3.0 inches). The bores for the sucker ports 34 are preferably tangent to the surface of the arch 33. The arch 33 directs the cardiotomy blood vertically downward into a first interior space 90 with minimal disturbance. The gradual shape of the arch 33 causes bubbles in the cardiotomy blood stream to rise to the surface. The bubbles may be broken when they contact pre-filter defoamer material 64 as the cardiotomy blood flows along the arch 33. Alternatively, the bubbles in the cardiotomy blood collect at the bottom of the separation chamber 37, where they are broken or popped by the pre-filter defoamer material 64. The cardiotomy blood preferably does not flow through the pre-filter defoamer material 64. The present cardiotomy manifold 36 can process at least six liters/minute (such as for example during sucker bypass) for an indefinite period of time.

Cardiotomy blood enters the modular blood treatment system 20 through the sucker ports 34 and cardiotomy manifold 36, and flows into the first interior space 90. The portion of the chamber 26 between the first blood treatment media assembly 72 and the second blood treatment media assembly 82 defines a second interior space 92. The venous blood stream and filtered cardiotomy blood stream are collected in the second interior space 92 prior to defoaming.

Figure 3:
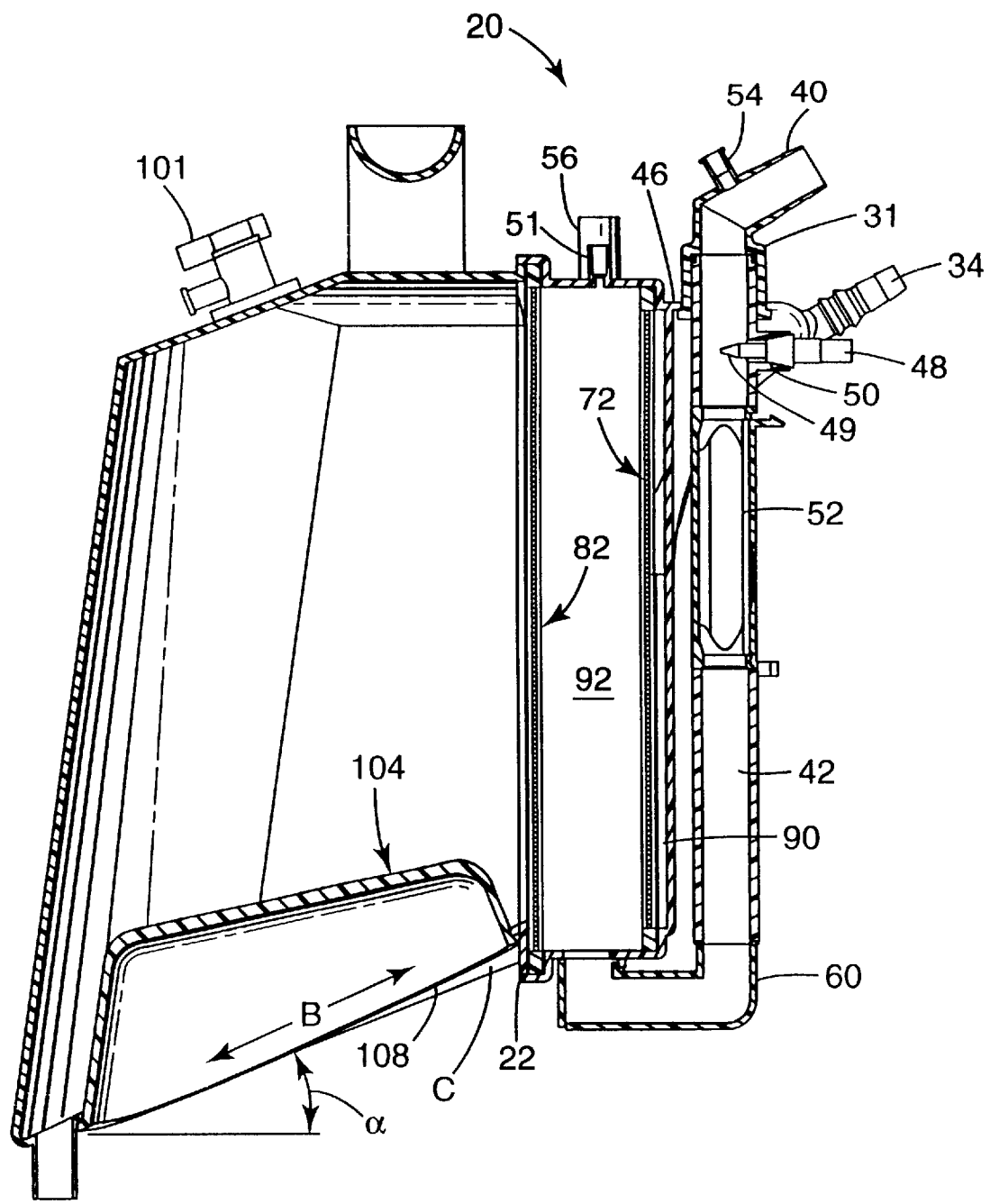
FIG. 3 is a side sectional view of the modular blood treatment system of FIG. 1.

As best illustrated in FIG. 3, a swiveling venous inlet connector 40 on a venous drop tube 42 is fluidly connected to the cartridge 22. A fluid line (not shown) carries the venous return stream from the patient to the inlet connector 40. A 30–70 durometer, silicone O-ring 31 is preferably interposed between the venous inlet connector 40 and the venous drop tube 42. The venous inlet connector 40 preferably is arranged at between 30 and 60 with respect to the venous drop tube 42 and has an outside diameter of 12.6 mm. A venous sampling luer site 54 is located on the venous inlet connector 40. The venous inlet connector 40 preferably includes a connector flange 44 that engages with a semicircular ledge 46 on the back of the blood treatment cartridge 22. An opening 50 is provided in the venous drop tube 42 for receiving a temperature sensor 48. The stainless steel thimble 49 is preferably hermetically sealed across the opening 50 in fluid communication with the venous return stream. The temperature sensor 48 is preferably located within the thimble 49.

Figure 6:
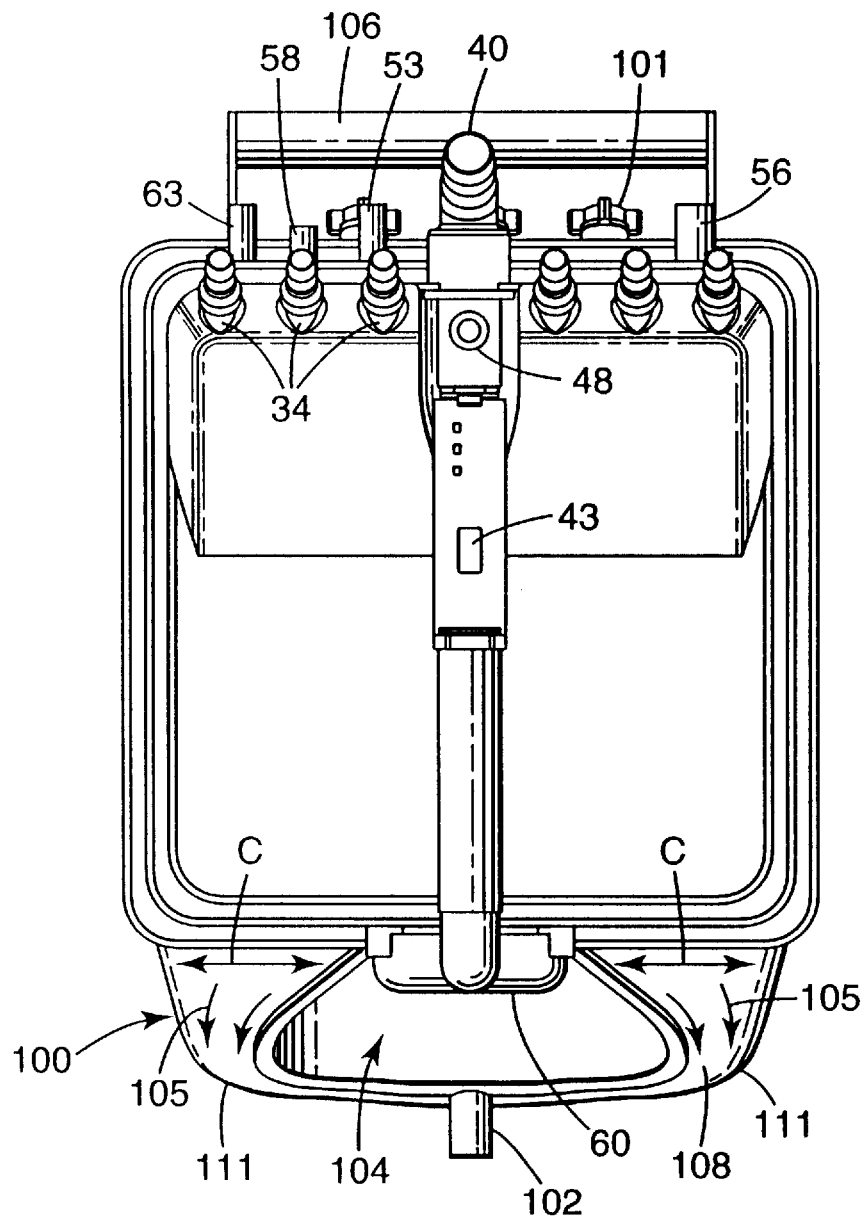
FIG. 6 is a back view of the modular blood treatment system of FIG. 1.

The venous drop tube 42 preferably includes a cuvette tube 52 with a sensor window 43 (see FIG. 6). The sensor window 43 typically interfaces with an infrared sensor for measuring oxygen content and hematocrit in the venous return stream. A suitable cuvette tube 52 is available from CDI, a division of Minnesota Mining and Manufacturing Company, located in Tustin, Calif., under product designation CDI 100.

Figure 2:
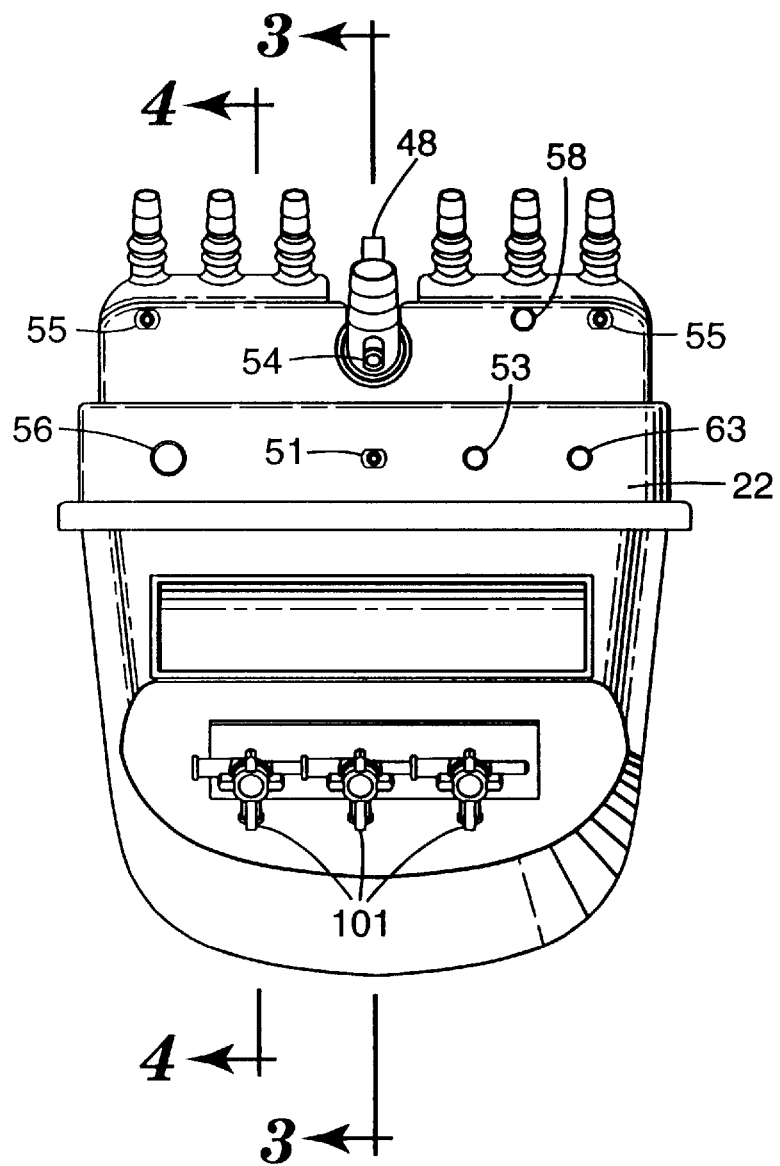
FIG. 2 is a top view of the modular blood treatment cartridge system of FIG. 1.

Turning to FIG. 2, the blood treatment cartridge 22 preferably includes a series of ports along the top surface. A pair of filtered luer ports 55 provide access to the cardiotomy manifold 36. A 6.35 mm (0.25 inch) diameter prime port 58 in fluid communication with the cardiotomy manifold 36 is provided for priming the modular blood treatment system 20. A vent port 53 is provided for releasing excess pressure from the chamber 26 during usage. The vent port 53 is preferably in fluid communication with the second interior space 92, although it will be understood that a series of vents may be provided for some applications. A recirculation port 63 allows priming fluid, such as saline, to be recirculated between the modular blood treatment system 20 and an oxygenator (not shown) during the prime cycle. Finally a drug inlet port 51 provides access to the interior space 92 containing the venous return stream and the filtered cardiotomy blood stream. An exemplary oxygenator is shown in U.S. Pat. No. 5,149,318 (Lindsay) and U.S. Pat. No. 5,514,335 (Leonard et al.).

An auxiliary cardiotomy inlet 56 provides direct access to the chamber 92. In the event that the cardiotomy filter assembly 72 fails, a secondary filter assembly (not shown) for filtering the cardiotomy blood stream can be inserted into the blood circuit with minimal disruption to the surgery procedure. The filtered blood stream from the secondary filter assembly can then be directed to the chamber 92, thereby bypassing the failed filter assembly 72. An alternate system for handling medical fluids is shown in U.S. Pat. No. 5,254,080 (Lindsay).

As shown best in FIGS. 1 and 3, a prime bowl 60 is located at the bottom of the venous drop tube 42 in fluid communication with the interior space 92 through an elongated inlet 59. Blood collects in the prime bowl 60 below chamber 26. In the event that the blood pumps fail, allowing blood in the drop tube 42 to travel is backwards through the blood circuit, the prime bowl 60 operates as a trap to prevent air in the blood treatment system 20 from entering the venous blood stream. A blood trap is shown in U.S. Pat. No. 5,282,783 (Lindsay) and U.S. Pat. No. 5,403,273 (Lindsay).

The prime bowl 60 also operates as a velocity reducer. The prime bowl 60 preferably has a cross-section about four to six times greater than the cross section of the drop tube 42. Consequently, the velocity of the venous return stream in the drop tube 42 is reduced to about 15–20% of its original velocity. For example, if the modular blood treatment system is operating at seven liters/min, the velocity of the venous return stream is reduced from 55 meters/min. to about 8.3 meters/min. The reduced velocity minimizes splashing, foam-creating turbulent flow and contact with the air. The elongated shape of the elongated inlet 59 cause the venous return stream to exit the prime bowl 60 primarily laterally toward the edges 22A, 22B of the blood treatment cartridge 22 so that blood stasis in these regions is minimized.

A series of support veins 62 are formed along the chamber 26 proximate the cardiotomy manifold 36 for supporting the pre-filter defoamer material 64. The pre-filter defoamer material 64 serves to dissipate bubbles on the surface of the cardiotomy blood stream without directly interrupting the flow. Although the pre-filter defoamer material 64 is generally a planar sheet folded as shown best in FIG. 4, it will be understood that a variety of shapes are possible, such as a triangular cross-section. A pre-filter ledge 68 is located on each of the support veins 62 for retaining the pre-filter defoamer material 64 proximate the sucker ports 34. The pre-filter defoamer material 64 is preferably inserted into the chamber 26 along a build axis "A".

A filter seal ledge 70 is located around the perimeter of the chamber 26 adjacent to the cardiotomy manifold 36. The filter seal ledge 70 is configured to receive a first blood treatment media assembly 72. The first blood treatment media assembly 72 is preferably a filtration media 74 supported by a media frame 76. The media frame 76 is preferably inserted into the chamber 26 along the build axis "A" to engage with the filter seal ledge 70 adjacent to the cardiotomy manifold 36. As discussed above, the first blood treatment media assembly 72 and cardiotomy manifold forms a first interior space 90 (see FIG. 3).

A defoamer seal ledge 80 is located along the perimeter of the interior space 26 for receiving a second blood treatment media assembly 82. The second blood treatment media assembly 82 is preferably a defoamer media 84 retained in a media frame 86. A support screen 85 may optionally be positioned on one or both sides of the defoamer media 84. The media frame 86 is preferably configured to engage with the defoamer seal ledge 80. The filter seal ledge 70 preferably defines a smaller perimeter than the defoamer seal ledge 80 so that the blood treatment media assemblies 72, 82 can be easily inserted into the blood treatment cartridge 22 along the build axis "A." The media 74, 84 may be retained in the frames 76, 86 by a urethane potting resin, mechanical gasket, UV cured adhesive, or a variety of other methods. The first and second blood treatment media are preferably planar or some other discontinuous configuration that does not create enclosures that can not be viewed by the medical staff. Discontinuous configuration generally refers to media material that does not form a self-contained enclosure or pocket, such as a cylinder or pouch configuration.

It will be understood that additional seal ledges may be included along the perimeter of the chamber 26 for receiving additional blood treatment media. The perimeter of the seal ledges preferably increases in size closer to the cartridge flange 28 so that they can be automatically stacked in the chamber 26 along the build axis "A." In an alternate embodiment, a single seal ledge is provided proximate the cardiotomy manifold 36. Spacers may then provided along the perimeter of the chamber 26 to maintain the appropriate separation between the blood treatment media 72, 82.

The front blood reservoir 32 preferably includes a blood storage section 100 and a drain port 102. A handle 106 is preferably provided along the top of the front blood reservoir 32. A series of alternate sampling ports 101 may be provided along the top of the reservoir 32. It will be understood that the handle 106 may be located along any surface of the modular blood treatment system 20. The handle 106 may be used for carrying the modular blood treatment system 20, retaining sampling syringes or sampling lines during use. The blood storage section 100 preferably has a capacity of 2.0–4.0 liters. The treated blood exits the modular blood treatment system 20 via the drain port 102 prior to further handling and treatment, such as regulation of carbon dioxide content, oxygen content and temperature. The blood is ultimately returned to the patient through an aortic cannula inserted into the aorta distal to the heart.

A diverter dome 104 may optionally be included in the front blood reservoir 32. The diverter dome 104 reduces the volume retained in the storage section 100 proximate the outlet port 102. In the preferred embodiment, the volume of the storage section 100 below the level of the bottom of the second filter media assembly 82 is approximately 300 cc. The diverter dome 104 is configured to define funnel-shaped flow channels shown by arrows 105 on either side toward the outlet port 102 (see FIG. 6). The diverter dome 104 preferably has a radius of curvature along a leading edge 109 of about 9.53 mm (0.375 inches). The radius along the leading edge 109 blends into a radius of about 6.35 cm (2.5 inches) and then 7.62 cm (3.0 inches) along the sides toward the trailing edges 107. The radius of curvature for the trailing edges 107 is about 23.9 mm (0.94 inches). The portion of the diverter dome 104 about 22.6 mm (0.89 inches) long between the two trailing edges 107 is straight. The diverter dome 104 has an overall length of about 12.6 cm (4.95 inches). The distance between the two trailing edges 107 is about 10.1 cm (4.0 inches).

As best seen in FIGS. 3 and 6, bottom surface 108 of the funnel-shaped flow channels 105 defines a first flow axis B extending downward at an angle α of about 20 to 24 from horizontal toward the outlet port 102. The bottom surface 108 preferably defines a second flow axis C having a downward taper of approximately 3 to 7 extending away from the diverter dome 104 and generally perpendicular to the first flow axis B. The resulting flow is away from the diverter dome 104 toward the curved edges 111 on either side of the outlet port 102. The compound curves along the bottom surface 108 results in a low-turbulent, sheet-flow of blood through the front blood reservoir 32.

Figure 7:
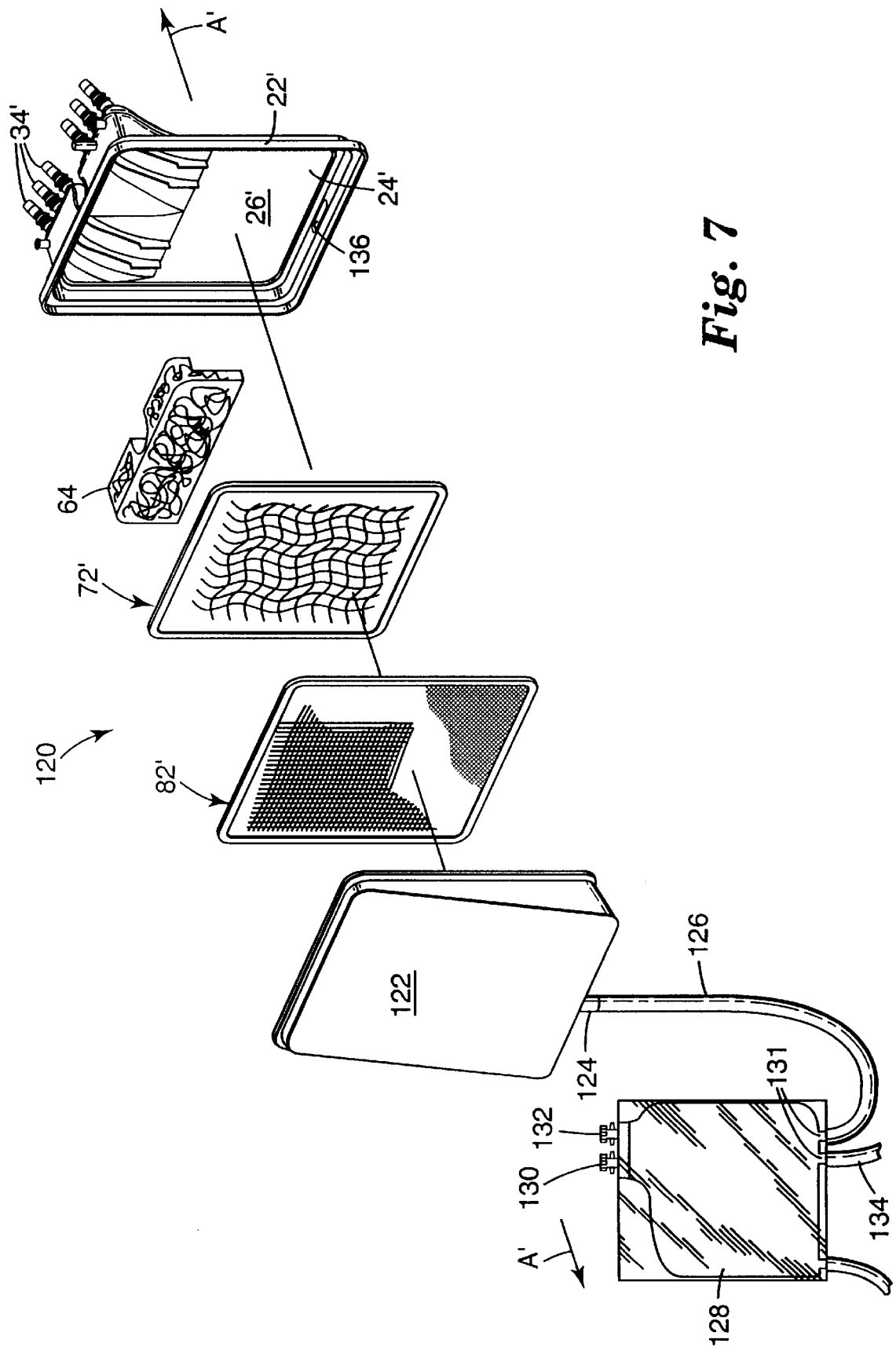
FIG. 7 is an exploded view of an alternate modular blood treatment system for cardiotomy blood.

FIG. 7 is an exploded view of an alternate modular blood treatment system 120 for treating primarily cardiotomy blood. A front blood reservoir 122 seals the blood treatment media receiving opening 24' on the blood treatment cartridge 22'. The cartridge 22' is further discussed below in connection with FIGS. 8–10. It will be understood that the front blood reservoir 122 may be used with the cartridge 22 shown in FIGS. 1–6. The modular blood treatment system 120 is preferably assembled along the build axis A', as discussed herein.

The front blood reservoir 122 preferably has minimal volume for retaining blood. An outlet port 124 diverts the treated blood through a tubing 126 to a secondary blood storage reservoir 128, such as a flexible pouch or bag. The blood reservoir 128 preferably includes a pair of valves 130, 132 for venting air and adding drugs. The venous return stream is delivered directly to the blood reservoir 128 by a venous input line 134, thereby bypassing the modular blood treatment system 120. Check valves 131 may optionally be provided in the tubes 126, 134. A cap 136 is preferably located in the venous inlet to seal the chamber 26'. In the configuration of FIG. 7, the modular blood treatment system 120 treats only the cardiotomy blood drawn in through the sucker ports 34'.

Figure 8:
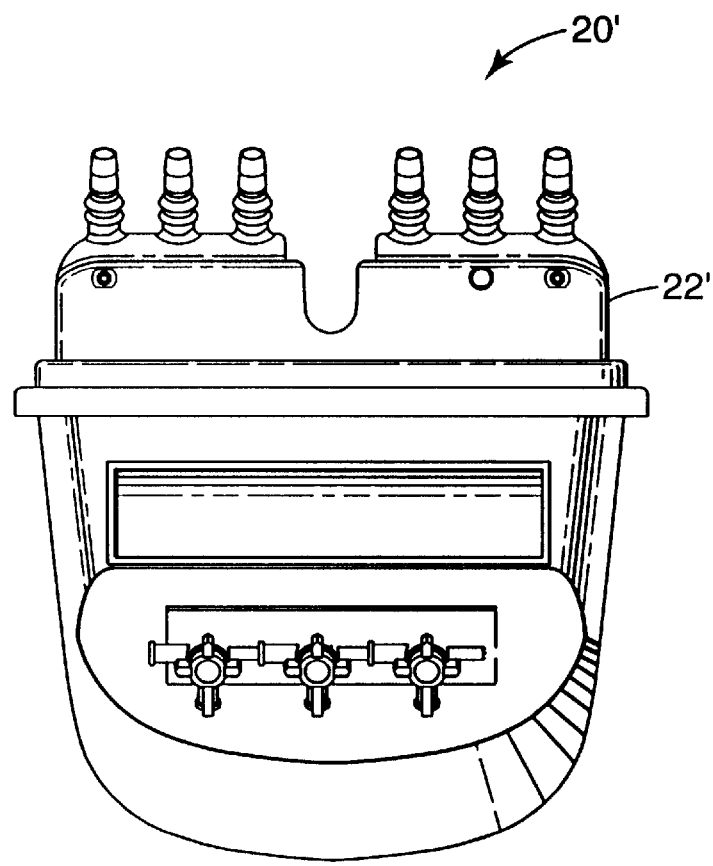
FIG. 8 is a top view of an alternate cardiotomy blood treatment system.
Figure 9:
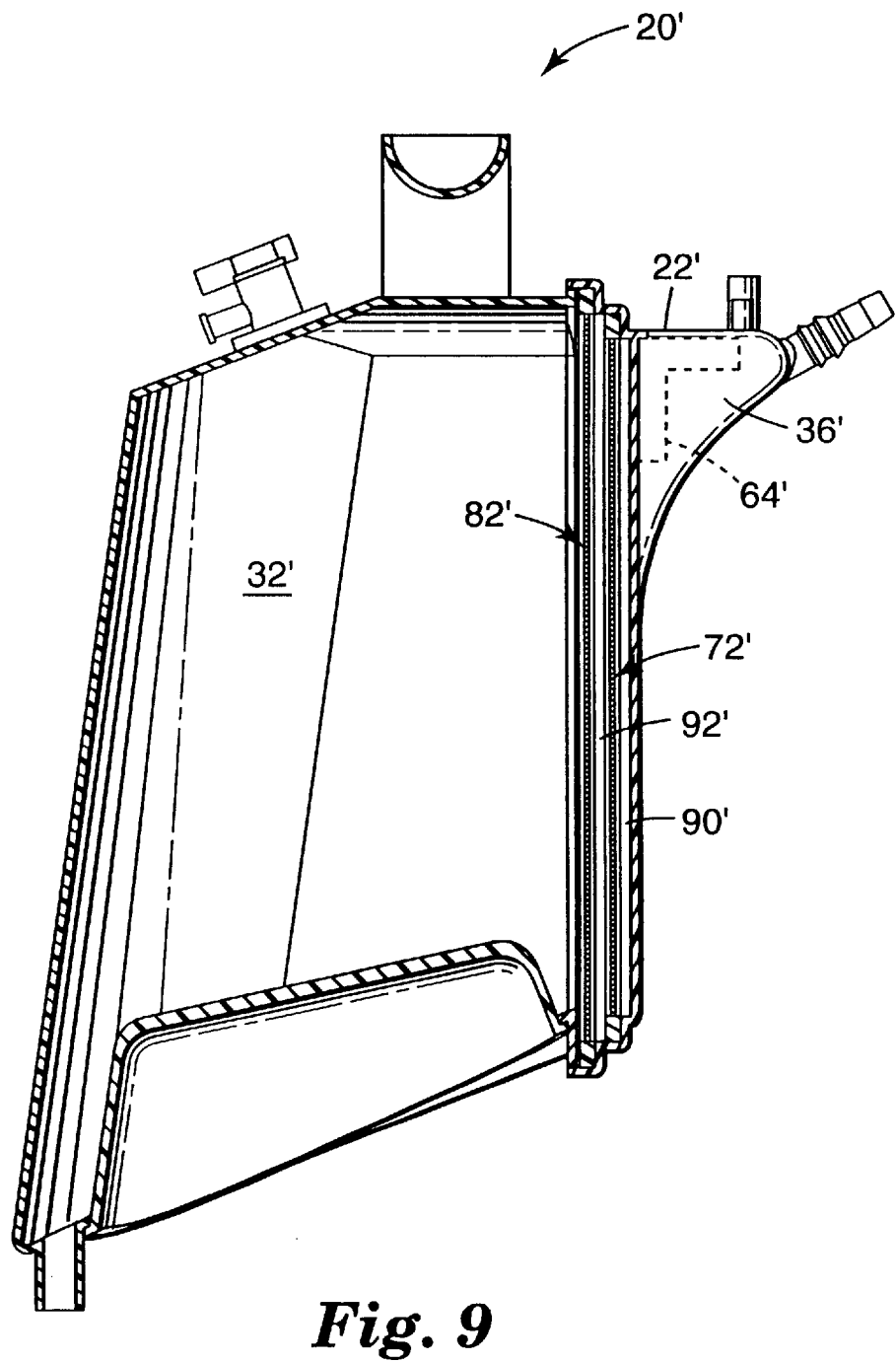
FIG. 9 is side sectional view of the cardiotomy blood treatment system of FIG. 8.
Figure 10:
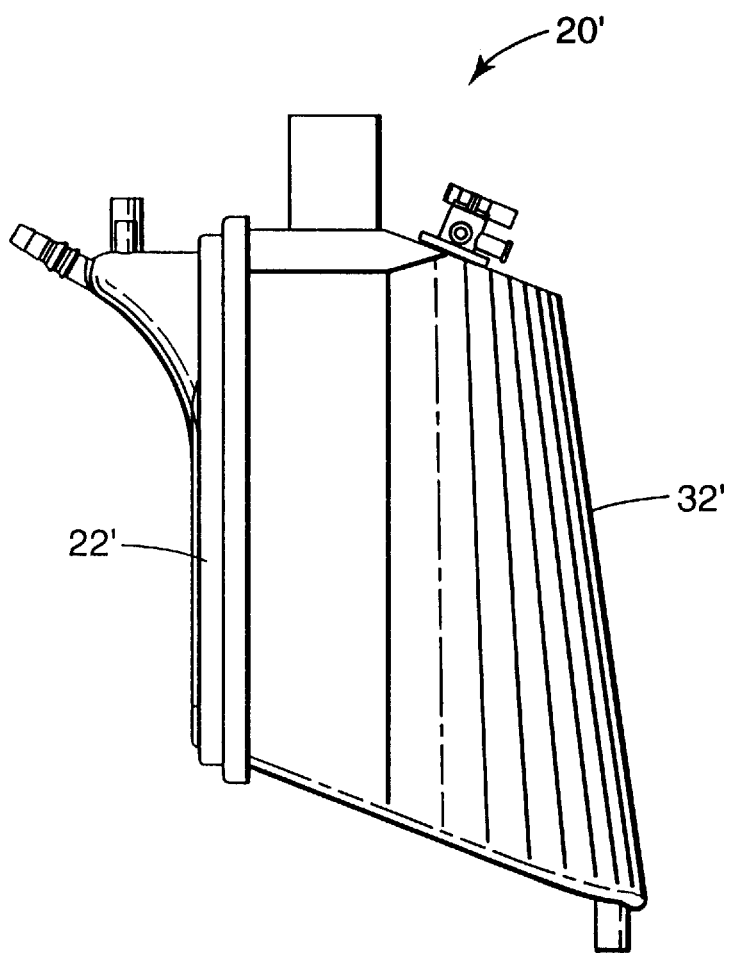
FIG. 10 is side view of the cardiotomy blood treatment system of FIG. 8.

FIGS. 8–10 illustrate the cardiotomy blood treatment cartridge 22' of FIG. 7 used with the front blood reservoir 32 of FIG. 1. Since the venous return stream is not directed through the modular blood treatment system 20', the chamber 92' is significantly compressed as compared to the chamber 92 in FIG. 4. The compressed chamber 90' reduces the initial break through volume to prime the system 20'. The operation of the cardiotomy manifold 36', the first and second blood treatment media assemblies 72', 82' and the front blood reservoir 32' are substantially the same as discussed above.

The pre-filter defoamer material 64 is preferably constructed of an open cell, blood compatible, synthetic polymeric foam, such as a reticulated polyurethane foam, that collapses blood foam into liquid blood. The pre-filter defoamer material 64 preferably has 5–20 pores per inch (PPI) and most preferably 10 pores per inch. The pre-filters are preferably treated with an anti-foam compound such as silicone.

The filtration media may be constructed of fibrous polyester depth filter. Commercially available filtration media include Dacron polyester felt having a mean aperture size in the range of about 20 to 50 microns, and preferably 30 microns. The filtration media 74 is alternatively constructed of a pleated depth media with a pore size of about 20–40 microns and most preferably with pore size of 30 microns.

The defoamer media may be constructed from a woven screen of nylon, polyester or polypropylene. The defoamer media 84 is preferably a mesh with 10–40 pores per inch and most preferably 26 pores per inch. The defoamer media is preferably coated with silicone. The defoamer media 84 is preferably supported on the downstream side by a support screen 85 having pore sizes of about 300–400 microns. A suitable silicone coated, reticulated polyurethane foam with 26 PPI is available from Lydall Westex, located in Hamptonville, N.C.

The modular blood treatment systems 20, 20', 120 are preferably molded from a clear thermoplastic such as polycarbonate or PET-G (glycol modified polyethylene terephthalate). In a preferred embodiment, the components have a nominal wall thickness of about 2.16 mm to 2.29 mm (0.085 inches to 0.090 inches). The components of the modular blood treatment systems 20, 20', 120 are preferably treated with heparin. Heparin is an acid mucopolysaccharide that acts as an anti-thrombin, anti-thromboplastin, and an anti-platelet factor to prolong clotting time of whole blood.

The present modular blood treatment systems 20, 20', 120 are designed so that the blood stream is easily visible to the medical staff at all times. Visibility of the blood stream is necessary to monitor for potential filter failure, blood stasis, debris, color and other factors. In particular, the drop tube 42, the blood treatment cartridge 22 and the front blood reservoir 32 are preferably constructed of a clear plastic material. Consequently, all sides of the pre-filter defoamer material are visible from either the top, back, bottom or sides of the cartridge 22. The chambers 90, 90', 92, 92' are visible around the perimeter of the cartridges 22, 22' (see FIGS. 3, 4 and 9). The contents of the front blood reservoirs 32, 32', 122 are visible from the front or sides thereof.

Figure 11:
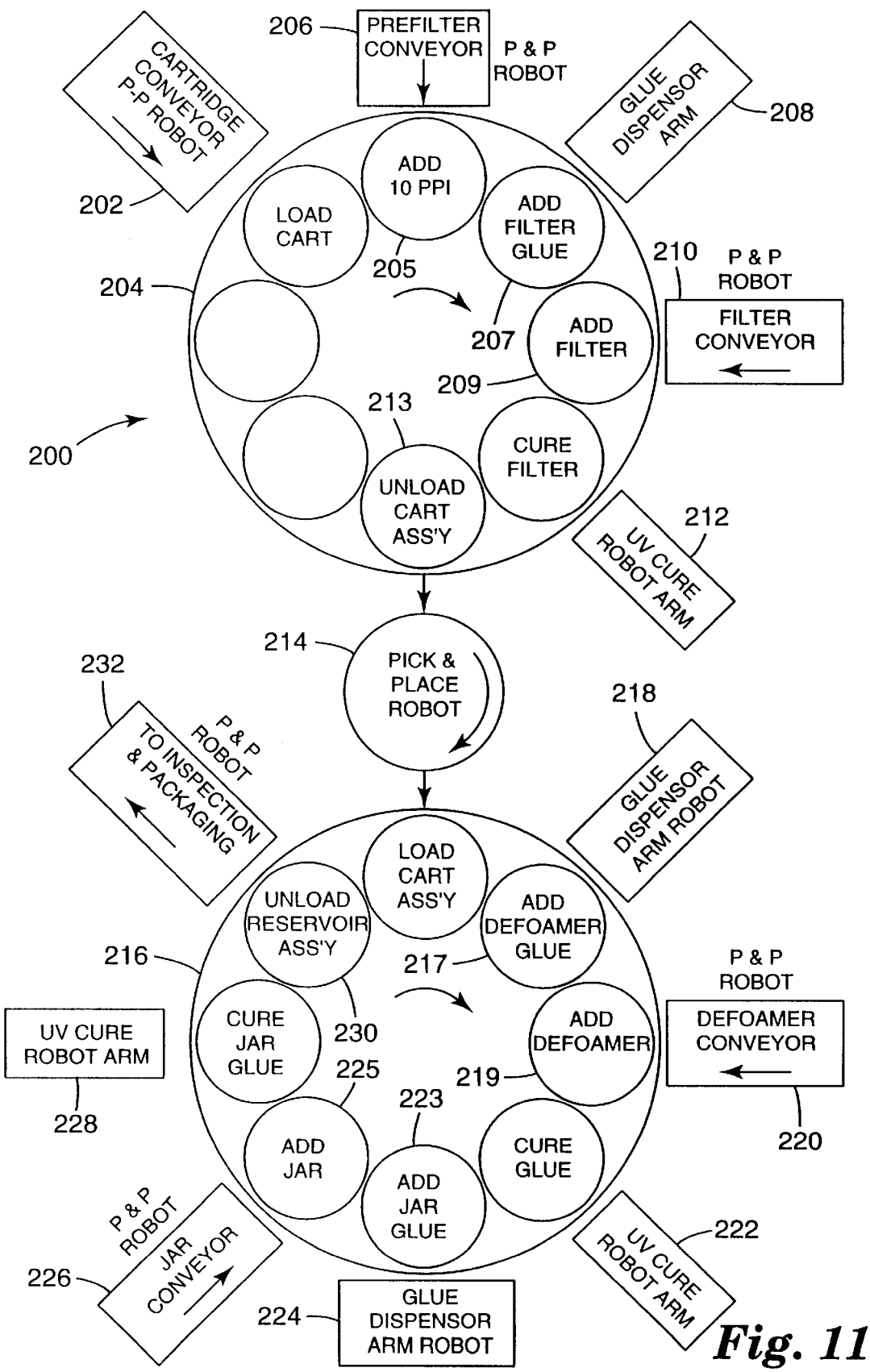
FIG. 11 is a schematic view of a method of assembling the present modular blood treatment system.

FIG. 11 is a schematic illustration of a preferred method 200 of assembling the present modular blood treatment systems 20, 20', 120. A pick and place robot 202 locates a blood treatment cartridge on an assembly carousel 204. The carousel 204 rotates to a second station 205 where a pick and place robot 206 installs a pre-filter foam material in the blood treatment cartridge along the build axis "A." A glue dispenser arm 208 applies a bead of glue along the filter seal ledge at station 207 in preparation for insertion of the first blood treatment media. The carousel moves the assembly to station 209 where pick and place robot 210 inserts the first blood treatment media into the chamber along the build axes A or A'. The glue is then cured at a UV curing station 212. The carousel 204 then moves the partially assembled blood treatment system to an unload cart 213 where a pick and place robot 214 transfers the assembly to a second carousel 216.

A glue dispenser arm 218 at station 217 applies a bead of glue along the defoamer seal ledge in preparation for insertion of the second blood treatment media. A pick and place robot 220 at station 219 installs the second blood treatment media along a build axes A or A' into the chamber. The glue is cured at a UV curing station 222. The carousel 216 then rotates to a second glue dispenser arm 224 at station 223 where glue is applied along the cartridge flange in preparation for installation of the front blood reservoir 32. A pick and place robot 226 at station 225 installs the front blood reservoir along a build axis A or A'. The glue is cured by a UV cure robot arm 228. The carousel 216 then rotates to station 230 where a pick and place robot 232 removes the modular blood treatment system 20, where it is forwarded for inspection and packaging.

The structure of the modular blood treatment system permits each of the components to be inter-engaged along a single build axis, thus facilitating automated assembly. Additionally, the minimal number of components renders automated assembly a cost-effective alternative. Automated assembly provides a number of key advantages for medical devices of this type. First, assembly is extremely accurate and repeatable. Secondly, the modular nature of the blood treatment system permits a variety of blood treatment media to be substituted automatically during the assembly process. The automated assembly process permits the type of blood treatment media installed in a particular modular blood treatment system to be accurately tracked and recorded.

All patents and patent applications referred to above are hereby incorporated by reference.

The present invention has now been described with reference to several embodiments described herein. It will be apparent to those skilled in the art that many changes can be made in the embodiments without departing from the scope of the invention. Thus, the scope of the present invention should not be limited to the structures described herein, but only to structures described by the language of the claims and the equivalents to those structures.

What is claimed is:

1. A method of assembling a blood treatment system along a single build axis, the method comprising:

providing a blood treatment cartridge having a chamber, a blood-treatment-media-receiving opening defining an entrance to the chamber, a cardiotomy manifold in fluid communication with the chamber, and at least one cardiotomy blood sucker port in fluid communication with the cardiotomy manifold;

inserting a first generally planar blood treatment media along the build axis through the blood-treatment-media-receiving opening into the chamber, the first blood treatment media dividing the chamber into first and second interior spaces, with the cardiotomy manifold in fluid communication with the first interior space;

inserting a second generally planar blood treatment media along the build axis through the blood-treatment-media-receiving opening of the blood treatment cartridge to enclose the second interior space;

placing a blood outlet section against the blood treatment cartridge along the build axis; and sealing the blood outlet section to the blood treatment cartridge to form a housing enclosing the blood-treatment-media-receiving opening, the blood outlet section having an outlet port.

2. The method according to claim 1 further comprising forming the blood treatment cartridge and blood storage section of transparent plastic material, and configuring the housing such that substantially the entire blood flow path is visible.

3. The method according to claim 1 wherein the blood treatment cartridge includes at least one ledge in the chamber configured and positioned to engage the first blood treatment media to limit insertion of the first blood treatment media into the chamber, the step of inserting a first generally planar blood treatment media along the build axis through the blood-treatment-media-receiving opening into the chamber further including:

engaging the at least one ledge in the chamber with the first blood treatment media to limit insertion of the first blood treatment media into the chamber.

4. The method according to claim 3 wherein the ledge constitutes a first ledge, the blood treatment cartridge further including a second ledge in the chamber between the blood-treatment-media-receiving opening and the first ledge and configured to engage the second blood treatment media to limit insertion of the second blood treatment media into the chamber, the second ledge defining a perimeter larger than the first ledge and permitting the first blood treatment media to be inserted into the chamber farther than the second ledge;

the step of inserting a first generally planar blood treatment media along the build axis through the blood-treatment-media-receiving opening into the chamber further including inserting the first blood treatment media into the chamber farther than the second ledge; and the step of inserting a second generally planar blood treatment media along the build axis through the blood-treatment-media-receiving opening of the blood treatment cartridge to enclose the second interior space further including engaging the second ledge in the chamber with the second blood treatment media to limit insertion of the second blood treatment media into the chamber.

5. The method according to claim 1 further comprising providing a venous blood inlet in fluid communication with the second interior space of the chamber, and spacing the venous blood inlet along the build axis from the cardiotomy manifold.

6. The method according to claim 5 further comprising:

forming the first blood treatment media as a filtration media for filtering cardiotomy blood entering the system through the cardiotomy blood sucker port;

forming the second blood treatment media as a defoamer media for defoaming venous blood entering the system through the venous blood inlet and cardiotomy blood filtered by the filtration media; and inserting a pre-filter defoamer into the chamber for defoaming cardiotomy blood entering the first interior space from the cardiotomy blood sucker port before that blood is filtered by the filtration media.

7. The method according to claim 6 wherein the step of forming the first blood treatment media as a filtration media for filtering cardiotomy blood entering the system through the cardiotomy blood sucker port further includes forming the filtration media with an average pore size of about 20 to 40 microns.

8. The method according to claim 6 wherein the step of forming the first blood treatment media as a filtration media for filtering cardiotomy blood entering the system through the cardiotomy blood sucker port further includes forming a first frame extending around a perimeter of the filtration media, and the step of forming the second blood treatment media as a defoamer media for defoaming venous blood entering the system through the venous blood inlet and cardiotomy blood filtered by the filtration media further includes a second frame extending around a perimeter of the defoamer media.

9. The method according to claim 5 wherein the step of providing a blood treatment cartridge having a chamber, a blood-treatment-media-receiving opening defining an entrance to the chamber, a cardiotomy manifold in fluid communication with the chamber, and at least one cardiotomy blood sucker port in fluid communication with the cardiotomy manifold further includes:

forming the cardiotomy manifold to define a downward curving ledge extending from the cardiotomy blood sucker port to the first interior space, the downward curving ledge having a radius of about 2.5 to 7.6 cm, the cardiotomy blood sucker port extending along a tangent to the downward curving ledge;

forming a plurality of support veins on the cardiotomy manifold for supporting a pre-filter defoamer; and forming the venous blood inlet to include drop tube and a velocity-reducing prime bowl downstream of the drop tube for directing a portion of the blood flow path outwardly toward the walls of the blood treatment cartridge and decelerating the blood flow, the prime bowl having a generally elongate cross-section at least four times greater than the cross-section of the drop tube;

the method further comprising supporting the pre-filter defoamer on the plurality of support veins.

10. The method according to claim 1 wherein the step of sealing the blood outlet section to the blood treatment cartridge to form a housing enclosing the blood-treatment-media-receiving opening further includes:

engaging a perimeter of the blood-treatment-media-receiving opening of the blood treatment cartridge with the blood outlet section for a snap-fit.

11. The method according to claim 1 further comprises forming a blood storage chamber with the blood outlet section.

12. The method according to claim 11 further comprising forming a blood diverter within the blood storage chamber forming a pair of funnel-shaped blood flow channels diverging from one another as the channels extend from the blood-treatment-media-receiving opening toward the outlet port, and a pair of converging blood flow channels extending front the funnel-shaped blood flow channels to the outlet port.

13. The method according to claim 12 wherein the step of forming a blood diverter within the blood storage chamber forming a pair of funnel-shaped blood flow channels diverging from one another as the channels extend from the blood-treatment-media-receiving opening toward the outlet port, and a pair of converging blood flow channels extending from the funnel-shaped blood flow channels to the outlet port further includes;

forming the funnel-shaped and converging blood flow channels to define:

a first flow axis extending downwardly in the direction away from the blood-treatment-media-receiving opening at an angle of about 20 to 24 degrees with respect to horizontal; and a pair of second flow axii converging downwardly toward one another in the direction perpendicular to the first flow axis at an angle of about 3 to 7 degrees to the horizontal.

14. A blood treatment system comprising:

a housing defining a blood treatment chamber and blood storage chamber downstream of the blood treatment chamber, a cardiotomy manifold in fluid communication with the blood treatment chamber, at least one cardiotomy blood sucker port in fluid communication with the cardiotomy manifold, a venous blood inlet in fluid communication with the blood treatment chamber, and an outlet port in fluid communication with the blood storage chamber;

a blood filtration media assembly for filtering blood entering the blood treatment chamber through the cardiotomy blood sucker port;

a blood defoamer media assembly for defoaming blood entering the blood treatment chamber through the cardiotomy blood sucker port and venous blood inlet;

a blood diverter within the blood storage chamber forming, together with the housing, a pair of funnel-shaped blood flow channels diverging from one another as the channels extend from the blood-treatment-media-receiving opening toward the outlet port, and a pair of converging blood flow channels extending from the funnel-shaped blood flow channels to the outlet port, the funnel-shaped and converging blood flow channels defining:

a first flow axis extending downwardly in the direction away from the blood-treatment-media-receiving opening at an angle of about 20 to 24 degrees with respect to horizontal; and a pair of second flow axii converging downwardly toward one another in the direction perpendicular to the first flow axis at an angle of about 3 to 7 degrees to the horizontal.

15. A blood treatment system according to claim 14 wherein:

the cardiotomy manifold defines a downward curving ledge extending from the cardiotomy blood sucker port to the first interior space, the downward curving ledge having a radius of about 2.5 to 7.6 cm, the cardiotomy blood sucker port extending along a tangent to the downward curving ledge;

the system further includes a pre-filter defoamer for defoaming cardiotomy blood entering the first interior space from the cardiotomy blood sucker port before that blood is filtered by the filtration media;

the cardiotomy manifold further including a plurality of support veins supporting the pre-filter defoamer; and the venous blood inlet includes drop tube and a velocity-reducing prime bowl downstream of the drop tube for directing a portion of the blood flow path outwardly toward the walls of the blood treatment cartridge and decelerating the blood flow, the prime bowl having a generally elongate cross-section at least four times greater than the cross-section of the drop tube.

* * * * *

UNITED STATES PATENT AND TRADEMARK OFFICE
CERTIFICATE OF CORRECTION

PATENT NO.: 5,871,693

DATED: February 16, 1999

INVENTOR(S): Erin J. Lindsay

It is certified that error appears in the above-identified patent and that said Letters Patent is hereby corrected as shown below:

Col. 12, line 2, "front" should read --from--.

Signed and Sealed this

Fourth Day of January, 2000

Attest:

Attesting Officer

*Acting Commissioner of Patents and Trademarks*